(12) United States Patent
Lopez et al.

(10) Patent No.: US 11,826,505 B2
(45) Date of Patent: Nov. 28, 2023

(54) DRAINAGE SYSTEM WITH O-RING

(71) Applicant: CareFusion 2200, Inc., San Diego, CA (US)

(72) Inventors: Carol Lopez, Santo Domingo (DO); James C. Kantola, Waukegan, IL (US)

(73) Assignee: CareFusion 2200, Inc., San Diego, CA (US)

( * ) Notice: Subject to any disclaimer, the term of this patent is extended or adjusted under 35 U.S.C. 154(b) by 609 days.

(21) Appl. No.: 16/704,359

(22) Filed: Dec. 5, 2019

(65) Prior Publication Data

US 2020/0108184 A1 Apr. 9, 2020

Related U.S. Application Data

(63) Continuation of application No. 14/788,198, filed on Jun. 30, 2015, now Pat. No. 10,532,135.

(51) Int. Cl.
*A61M 1/00* (2006.01)

(52) U.S. Cl.
CPC ............... *A61M 1/71* (2021.05); *A61M 1/60* (2021.05); *A61M 1/64* (2021.05); *A61M 1/66* (2021.05); *A61M 1/732* (2021.05)

(58) Field of Classification Search
CPC ............. A61M 1/0023; A61M 1/0001; A61M 1/0003; A61M 1/60; A61M 1/64; A61M 1/71; A61M 1/66
See application file for complete search history.

(56) References Cited

U.S. PATENT DOCUMENTS

| | | | | |
|---|---|---|---|---|
| 3,397,803 A | * | 8/1968 | Melton | B65D 41/32 215/256 |
| 3,707,239 A | * | 12/1972 | Harris, Sr. | F16K 13/00 215/313 |
| 4,675,010 A | | 6/1987 | Siposs et al. | |
| 6,328,718 B1 | | 12/2001 | Chiang et al. | |
| 6,507,494 B1 | | 1/2003 | Hutchison et al. | |
| 7,048,724 B2 | * | 5/2006 | Grossman | A61M 1/0003 604/319 |
| 7,749,741 B2 | | 7/2010 | Bullen et al. | |
| 9,011,407 B2 | | 4/2015 | Harig | |
| 10,532,135 B2 | * | 1/2020 | Lopez | A61M 1/86 |
| 2004/1006902 | | 6/2004 | Grossman et al. | |

(Continued)

OTHER PUBLICATIONS

Office Action dated May 31, 2021 pertaining to European Application No. 16739300.8.

(Continued)

*Primary Examiner* — Jessica Arble
(74) *Attorney, Agent, or Firm* — Dinsmore & Shohl LLP

(57) ABSTRACT

A drainage system, the drainage system comprising a container having an interior and a mouth, the mouth comprising an outer surface and an opening, a frangible seal covering the opening, a cap secured to the mouth and in fluid communication with a drainage line, the cap having an inner surface configured to engage with the outer surface of the mouth, an O-ring located at least partially between the outer surface of the mouth and the inner surface of the cap and configured to form a fluid seal between a space defined by the cap and the space located externally of the drainage system, and a retaining ring circumferentially engaging the cap.

19 Claims, 5 Drawing Sheets

(56) References Cited

U.S. PATENT DOCUMENTS

| | | | |
|---|---|---|---|
| 2007/0148756 A1* | 6/2007 | Bullen | C12M 45/02 |
| | | | 435/308.1 |
| 2009/0264705 A1 | 10/2009 | Cushner et al. | |
| 2012/0225175 A1 | 9/2012 | Lown | |
| 2016/0256615 A1 | 9/2016 | Poormand | |

OTHER PUBLICATIONS

Office Action pertaining to corresponding Chinese Patent Application No. 201610513712.2, dated Jun. 9, 2020.

International Preliminary Report on Patentability and Written Opinion of the ISA dated Jan. 2, 2018 for PCT Application No. PCT/US2016/039278 14pp.).

International Preliminary Report on Patentability and Written Opinion of the ISA dated Feb. 9, 2017 for PCT Application No. PCT/US2016/039278 14pp.).

* cited by examiner

DRAINAGE SYSTEM WITH O-RING

CROSS-REFERENCE

This application is a continuation of U.S. patent application Ser. No. 14/788,198, filed Jun. 30, 2015 entitled "Drainage System with O-Ring," the details of which are hereby incorporated by reference.

TECHNICAL FIELD

The present invention relates to the field of medical devices and, in particular, to a device useful for withdrawing and containing fluids from a patient body.

BACKGROUND

Body fluids may need to be withdrawn from a patient in the course of medical treatment. Two common medical procedures requiring fluid removal are thoracentesis and paracentesis.

In paracentesis, peritoneal fluid is aspirated from the abdomen. Typical patients have tense ascites resulting from liver disease and portal hypertension, which may cause discomfort, respiratory distress, and the formation and rupture of umbilical hernias. Paracentesis has been observed to provide quick and effective relief with few adverse side effects. Other treatment options, such as the use of diuretics, are available, but may not provide as effective relief as paracentesis. Additionally, many patients with ascites have renal impairment and cannot use the high doses of diuretics necessary to effectively treat the ascites. See "Large-Volume Paracentesis in Nonedematous Patients with Tense-Ascites: Its Effect on Intravascular Volume," Pinto et al., *Hepatology*, Vol. 8, No. 2, pp. 207-210, 1988. Relatively large volumes of fluid, such as five liters, may be withdrawn from a patient during one paracentesis procedure.

Many existing devices are capable of performing paracentesis. At its simplest, a paracentesis device need only include a hollow needle with one end inserted into the patient and the other end attached to a negative pressure device, such as a syringe or vacuum bottle. However, more specialized devices have been developed to allow safer, more comfortable, and more sanitary paracentesis. These devices may allow for body fluid to be dispensed into at least two containers, so that one container may be filled with fluid for diagnostic purposes and the other container may be filled with waste fluid. Another development has been the use of Kuss or Verres type needle assemblies, where a blunt drainage needle is attached to a retractile sharp introducer needle. This reduces the likelihood of the sharp needle damaging internal tissue during paracentesis. A further development is to drain body fluid through a blunt-tipped catheter introduced by a sharp introducing needle, which allows the sharp needle to be removed from the patient after a relatively quick introduction process and avoids the prolonged presence of a sharp needle in the body of the patient.

Problems may arise when drainage is diverted from one container to another if the drainage system is not airtight. Air could contaminate a sample or enter the body of the patient and cause injury. Known devices that are meant to be airtight have tubes and multiple containers attached to the devices which make the devices cumbersome and somewhat difficult to insert into the patient. Also, known devices require manipulation of a manual valve, such as a stopcock to work effectively. If the stopcock is not set at the proper setting, the device may admit air into the patient or otherwise malfunction. Problems also may arise in devices which allow a needle assembly to be withdrawn. Air must be prevented from entering the patient when the fluid is withdrawn. Also, body fluid must be prevented from leaking out of the device through the space formerly occupied by the needle assembly.

Thoracentesis is a procedure similar to paracentesis, except that effusion fluid is withdrawn from the pleural region instead of the abdomen. Normally, the pleural space contains approximately 5 to 20 ml of fluid. The fluid is the result of the hydrostatic-onctotic pressure of the capillaries of the parietal pleura. The turnover of the fluid in the pleural space is normally quite rapid, so that 5 to 10 liters of fluid move through the pleural space each day. A disruption in the balance between the movement of fluid into the pleural space and the movement of fluid out of the pleural space may produce excessive fluid accumulation in the pleural space. Pleural effusion is particularly common in patients with disseminated breast cancer, lung cancer or lymphatic cancer and patients with congestive heart failure, but also occurs in patients with many other forms of malignancy.

Pleural effusion may cause dyspnea, coughing, and chest pain, which diminish a patient's quality of life. Although pleural effusion typically occurs toward the end of terminal malignancies, such as breast cancer, it occurs earlier in other diseases. Therefore, relieving the clinical manifestations of pleural effusion is for real and extended advantage to the patient. For example, non-breast cancer patients with pleural effusion have been known to survive for years. See "Pleural Effusion in Cancer Patients," Izbicki et al., *Cancer*, October 1975, p. 1511.

There are several treatments for pleural effusion. If the patient is asymptomatic and the effusion is known to be malignant or paramalignant, no treatment may be required. Pleurectomy and pleural abrasion are generally effective in obliterating the pleural space, thus controlling the malignant pleural effusion. However, pleurectomy is a major surgical procedure associated with substantial morbidity and some mortality. Chemotherapy is generally disappointing; however, it may produce good responses for patients with lymphoma, breast cancer, or small-cell carcinoma. Another approach is to surgically implant a chest tube. However, such a tube is painful to the patient, both when it is inserted and during the time that it remains in the pleural space. Improvements on the traditional chest tube are described in U.S. Pat. No. 5,484,401.

Despite other treatment options, thoracentesis remains the most common approach to removing pleural fluid. However, thoracentesis poses the danger of causing pneumothorax, a collapsed lung. Pneumothorax can be caused directly by puncturing a lung with a needle assembly or catheter tip or indirectly by allowing air to enter the pleural space. Normally, the pleural space is at negative pressure relative to the atmosphere, which helps keep the lungs expanded. If the atmosphere is allowed to communicate with the pleural space, the pleural space may no longer be at negative pressure and pneumothorax may result.

Thoracentesis devices have been developed to reduce the risk of pneumothorax and other similar problems that may result from the procedure. In general, these devices incorporate similar protections as do paracentesis devices. For example, U.S. Pat. No. 4,447,235 by Clarke discloses a thoracentesis device with a catheter introduced by a removable needle assembly, with a valve that closes upon removal of the needle assembly. The purpose of the valve is to prevent air from entering the body of the patient. U.S. Pat. Nos. 4,784,156, 4,832,044, 4,840,184, and 4,844,087 by Garg disclose similar devices with a manual valve that may be closed after withdrawal of the needle assembly. However, none of the previous devices allow for a truly fail-safe operation, as various valves must be properly set by the operator when changing from one drain port to another or when withdrawing the introducing needle assembly from the patient. Also, care must be taken to avoid accidental withdrawal of the introducing needle assembly, as in the disclosed devices where the needle assembly is not firmly attached to the remainder of the device. Further, the disclosed valves that allow for catheter drainage after removal of an introducing needle assembly rely on a single contact point. Due to the possibly dire consequences of a valve failure, such valves may not produce acceptably safe thoracentesis.

A Verres-type needle assembly that may be used for thoracentesis is disclosed in U.S. Pat. No. 5,334,159 by Turkel. While this reduces the risk of pneumothorax due to lung puncture, the Turkel device does not improve the safety of thoracentesis when the introducing needle assembly is withdrawn or solve the problems associated with multiple drainage ports. Thus there is a need for a safer and more reliable device that may be used for paracentesis and thoracentesis. Another device is described in U.S. Pat. No. 5,725,506 by Freeman, et al., which is incorporated by reference herein in its entirety.

Other difficulties with existing systems relate to manufacturing, storing and using the vacuum element. Syringes are sometimes used to generate the vacuum, but syringes are somewhat complicated to manufacture and use. An alternative vacuum source is a vacuum bottle. In that approach, a vacuum is created in an air-tight bottle at the manufacturing stage, and then the bottle is sealed. The bottle is then tapped at the time of use so that the vacuum can be applied to a drainage line to remove the undesired body fluids.

This is quite elegant in concept but somewhat difficult to implement perfectly in every individual unit. There is always some risk that the vacuum will be lost in transit before use, either by leaks, fractures or just air permeating through a plastic wall. Moreover, the loss of vacuum is not necessarily apparent to the user; a bottle with a perfect vacuum inside looks no different than a bottle of air, but the drainage efficacy of the unit may be diminished upon loss of vacuum before use or during use where the vacuum is wasted on pulling in air rather than exerting drainage effectively from the patient. Another problem is in tapping the bottle. This requires a system that pierces a vacuum seal but does not allow air to enter the bottle, except through the draw line. One such system is described in commonly owned U.S. Pat. No. 7,048,724 by Grossman et al, which is incorporated by reference herein in its entirety.

In known systems utilizing a vacuum bottle, a cap may be provided that acts as an interface between the bottle and a drainage line. In practice, it is typical for the junction of the cap and the bottle to be assembled with the use of an adhesive, such as a silicone adhesive gel. The silicone gel may act both to secure the cap to the bottle and to create a fluid seal at the junction.

Systems using a silicone adhesive have achieved positive results. However, silicone gel adhesive typically is expensive and manufacturing expenses associated with applying a silicone gel remain high. Further, it can be difficult to apply a precise amount of adhesive during the assembly process to achieve consistent securing and sealing that will patently maintain desired vacuum throughout the device live and usage. Silicone adhesives also typically can only dry and set one time, shortly after application, and therefore the system is generally shipped fully assembled, and it may be difficult to interchange the vacuum bottles at the medical facility.

In light of this background, it would be advantageous to provide an improved system utilizing a container, such as a vacuum bottle, connected to a drainage line that achieves sufficient securing and sealing between the container and cap without the need for the use of an adhesive.

BRIEF SUMMARY

A drainage system is provided. The drainage system comprises a container having an interior and a mouth with an outer surface and an opening, a frangible seal covering the opening, a cap secured to the mouth and in fluid communication with a drainage line, the cap having an inner surface configured to engage with the outer surface of the mouth, and an O-ring located at least partially between the outer surface of the mouth and the inner surface of the cap. The term "frangible" is here defined to include being able to be punctured, pierced, or otherwise interrupted. The O-ring may be configured to form a fluid seal between an area within the cap and the conditions external to the drainage system. The drainage system may further comprise a retaining ring circumferentially engaging the elastomeric cap.

In one embodiment, a spiked tube is positioned at least partially within the cap and is configured to pierce the frangible seal. An area within the cap and the interior of the container may be in fluid communication when the frangible seal is pierced. The cap may comprise a tapered widened body portion, and it may be formed from an opaque material.

In another embodiment, the mouth comprises a groove within the outer surface configured to seat the O-ring. Alternatively or in addition, the cap may comprise such a groove. The interior of the container may hold a vacuum. Further, a stop may be provided on the cap and a container may comprise a shoulder, wherein the stop is configured to contact the shoulder when the cap slides a first distance in the proximal direction into engagement with the mouth.

DETAILED DESCRIPTION OF THE DRAWINGS AND THE PRESENTLY PREFERRED EMBODIMENTS

Figure 1:
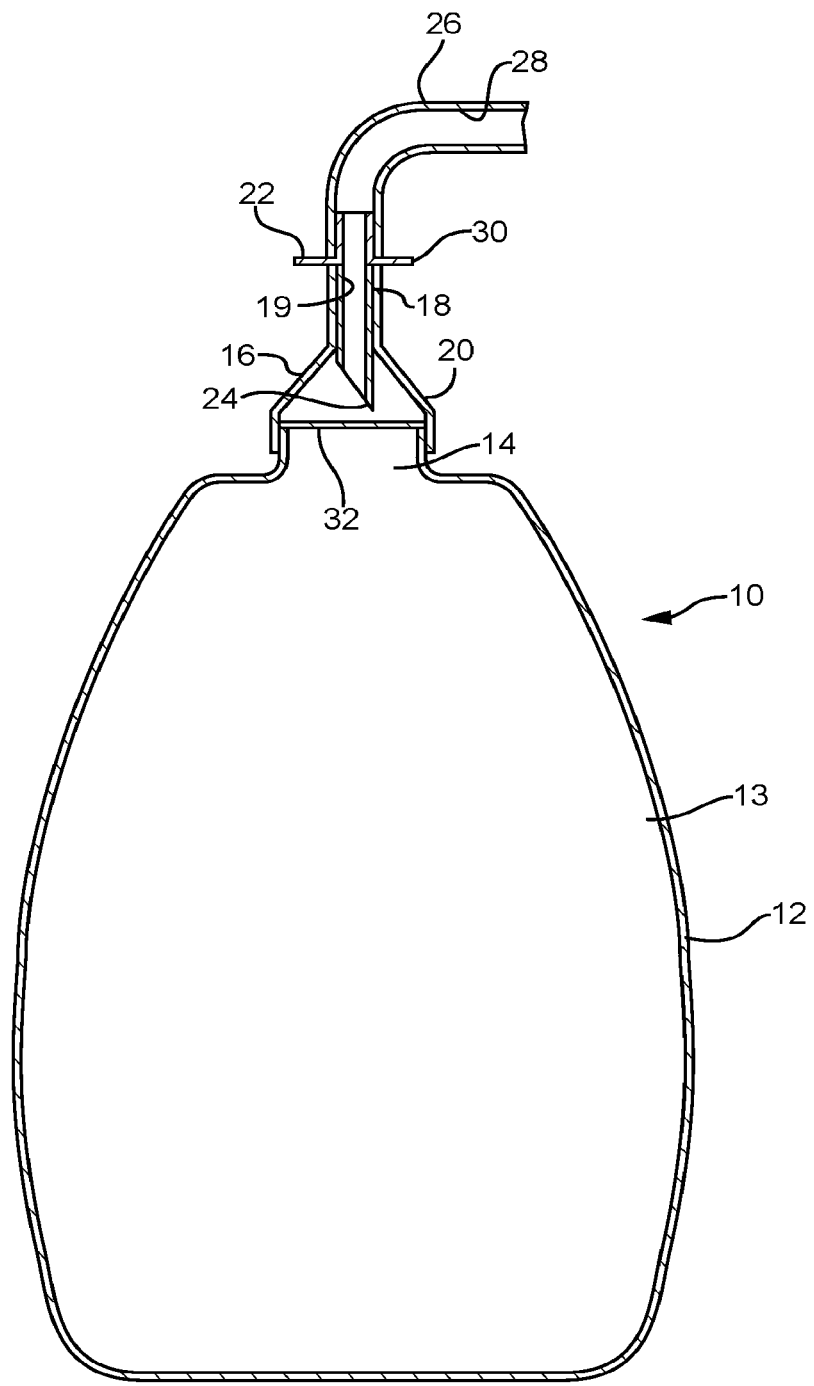
FIG. 1 shows a front cut-out schematic of one embodiment of a known drainage system.

Referring to FIG. 1, a container 12 comprises a mouth 14. Container 12 may, for example, be a bottle or a vacuum bottle. Covering the mouth 14 is a cap, such as an elastomeric cap 16, having a sleeve 18 at the upper (distal) end and a widened body 20 at the lower (proximal) end. Sleeve 18 of the elastomeric cap 16 may receive a spike 22 in a substantially air-tight seal between the exterior surface of spike 22 and a lumen of sleeve 18. In the present application, the term "proximal" is generally used to refer to an end or portion of the system that is nearest the container, while the term "distal" refers to an opposite end or portion that—in use—is near, or within, a patient being treated with the system.

The lower end of spike 22 terminates in a point 24. The upper end of spike 22 receives a drainage line 26 having a lumen 28 therethrough. As in the connection between spike 22 and the sleeve 18 of the elastomeric cap 16, the connection between spike 22 and drainage line 26 is preferably substantially air-tight. The spike 22 may also include a circumferential flange 30 to assist in manipulating spike 22 in relation to container 12 in the manner described below. A spike-lumen 19 may extend through spike.

A frangible seal 32 covers an opening at mouth 14 of the container 12 to seal container interior 13. Frangible seal 32 is preferably constructed of foil, mylar, or other substantially air-tight material, which may be elastomeric, and which may be attached to the edges of the mouth 14 of the container 12 to substantially prevent air from leaking into the container interior 13 to spoil the vacuum therein. This attachment can be accomplished by heat-sealing (as in, for example, direct heat, induction heat or vibration generated heating processes), by gluing or adhesion, or by any other suitable method.

The drainage system 10 may be packaged and shipped in a form that includes the container 12 sealed by the frangible seal 32, and with or without the other elements. More specifically, the drainage line 26 may be attached to the rest of the assembly at the time of use, or not. Alternatively, both the spike 22 and drainage line 26 may be attached to the assembly at the time of use, or not. Or the drainage line 26, spike 22 and elastomeric cap 16 may be attached to the assembly at the time of use, or not. In may be preferable, but is not necessary, to evacuate the container 12 before shipping.

To use the drainage system 10, it is assembled completely (if not already assembled completely). The distal end of drainage line 26 (not shown) is attached to a collection device that is placed into a target fluid space in the patient using a suitable medical technique. For example, the distal end of drainage line 26 can be placed in the pleural space of the patient to remove excess pleural fluid by means of a needle or catheter.

After engagement with a target fluid space is achieved, spike 22 is pushed toward the container 12 by applying a downward force to the flange 30. This deforms widened body 20 of elastomeric cap 16, which maintains the substantially air-tight seal between sleeve 18 and spike 22. The spike point 24 meets and pierces frangible seal 32, thereby transferring the vacuum from the container interior 13 into the space defined by the elastomeric cap 16 (or, more precisely, thereby drawing nearly all the small quantity of air from the space into the container interior to establish a vacuum in that space defined by the cap). This vacuum also extends through spike lumen 19 and into drainage line lumen 28. The effect is to draw fluid from the distal end of drainage line 26, through the drainage line 26 toward container 12, through the spike lumen 19, and into the container 12.

The rate of fluid withdrawal, and the magnitude of the vacuum applied to the patient, can be managed by using a clamp on drainage line 26. Opening the clamp slightly will produce a relatively modest vacuum at the distal end of drainage line 26 and a relatively slow rate of fluid withdrawal, while opening the clamp will produce a greater vacuum and faster rate of withdrawal.

It may be important to be able to verify at a glance that the vacuum in container interior 13 is intact before using the device. In the embodiment shown in FIG. 1, this can be accomplished by the appearance of the elastomeric cap 16. In its normal undistended position, the elastomeric cap will have a given shape that is easily discernible to the user. As the spike 22 pierces the frangible seal 32 to transfer the container 12 vacuum into the space defined by the elastomeric cap 16, atmospheric pressure on the exterior of the elastomeric cap 16 will tend to partially collapse it. This partial collapse will thus be apparent to the user, thereby verifying the bottle interior 13 vacuum.

As mentioned above, the vacuum indicator elements also serve to indicate a loss of vacuum over the course of the drainage procedure. More specifically, container 12 gradually fills as fluid is drawn out of the patient, through drainage line 26, and into container 12. This filling of the bottle of course lessens the vacuum, i.e., it increases the pressure to approach atmospheric. This loss of vacuum and resulting diminution in fluid flow could be mistaken for a sign that all the desired fluid has been withdrawn from the patient. The outcome would then be an incomplete procedure. This is prevented by the indicator elements. If the vacuum becomes insufficient over the course of the procedure, the indicator elements will so indicate, just as they indicate if the vacuum is insufficient at the outset of the procedure.

Figure 2:
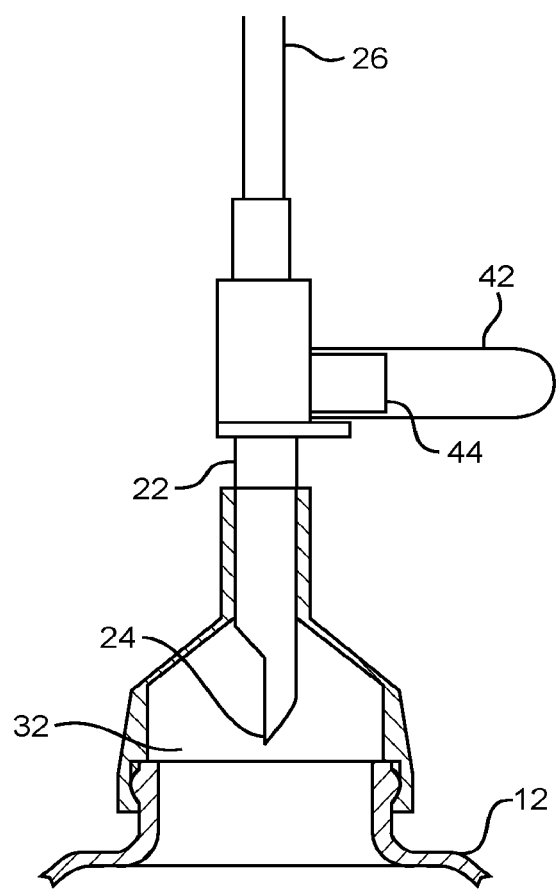
FIG. 2 shows a front cut-out partial sectional view of a known drainage system having a collapsible bulb.

An alternative embodiment of the drainage system 10 is shown in FIG. 2, in which the system for verifying the integrity of the vacuum is more elaborate. The overall configuration is essentially the same as the embodiment of FIG. 1 but with the addition of a collapsible bulb 42. Bulb 42 is in communication with the interior lumen of the spike 22 through a tubular fitting 44.

In this embodiment, before spike 22 pierces frangible seal 32 to transfer the vacuum into the spike 22 and drainage line 26, bulb 42 is in its natural undistended state. After spike 22 pierces frangible seal 32 to transfer the vacuum into spike 22 and drainage line 26, the differential pressure between the vacuum inside bulb 42 and the atmospheric pressure outside bulb 42 collapses or at least partially collapses bulb 42. This collapse or partial collapse is readily apparent to the user, thereby confirming the integrity of the vacuum.

Figure 3:
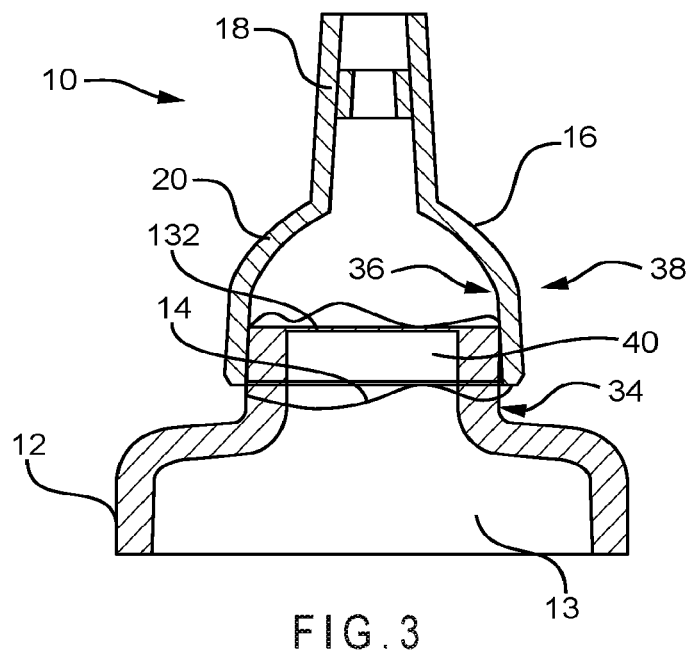
FIG. 3 shows a front cut-out partial view of a drainage system using a silicone adhesive at the junction of a cap and a container.

Referring to FIG. 3, elastomeric cap 16 is preferably engaged with (i.e., secured and sealed to) mouth 14 during a drainage procedure. In some embodiments, as depicted by FIG. 3, elastomeric cap 16 may be secured to mouth 14 at junction 38 with the use of an adhesive, such as silicone adhesive 40. The adhesive may be, for example, a commonly used adhesive such as NuSil MED-1037 Silicone Adhesive Sealant. Silicone adhesive 40 may be applied to an outer surface 34 of mouth 14 and/or to an inner surface 36 of widened body 20, and may operate both to secure elastomeric cap 16 in place with respect to container 12 and to maintain an air-tight seal at junction 38 between outer surface 34 and inner surface 36.

It may be advantageous for elastomeric cap 16 to be removable from container 12. For example, it may be necessary for a user to flush container 12 to dispose fluid contents from interior 13 shortly after a drainage procedure. In some instances, the disposal of the fluid contents must occur in a sanitary, controlled manner prior to disposing the container. Additionally, container 12 may be reusable after it is flushed and cleaned. Because the drainage procedure is often done in a patient home without immediate assistance of a physician or nurse, it is desirable for elastomeric cap 16 be sufficiently removable (e.g., easily removable) such that an at-home patient may perform the removing operation without trouble. This may limit the device to the use of a relatively low-pressure vacuum. For example, the pressure differential may be limited so that removal will require no more than a maximum of about 4 pounds of force (about 17 N).

In some embodiments, particularly when container 12 is reusable, it may be necessary for a user (such as a patient) to attach a new elastomeric cap 16 to container 12, potentially without the help of a medical professional. In the embodiment depicted by FIG. 3, it may be necessary for the user to apply an amount of silicon adhesive 40 to outer surface 34 and/or inner surface 36 to ensure elastomeric cap 16 properly engages with mouth 14 and to ensure sufficient sealing at junction 38 to contain a vacuum within the device.

Figure 4:
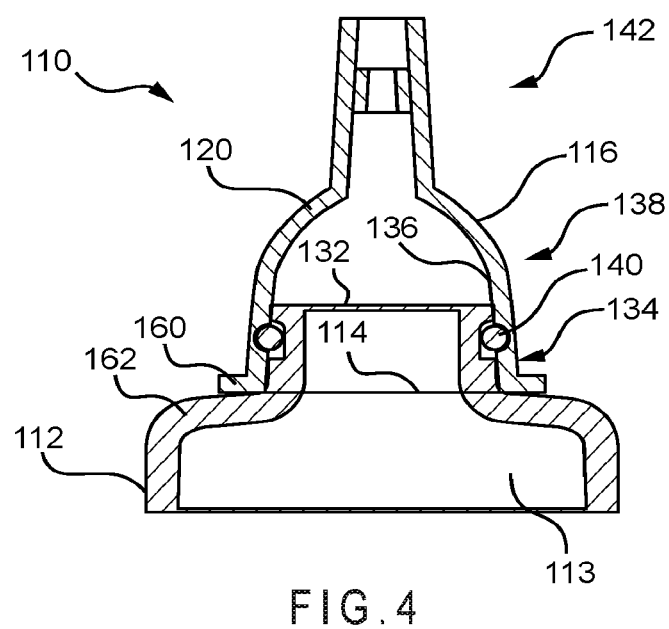
FIG. 4 shows a front cut-out partial view of a drainage system with an O-ring at the junction of a cap and a container
Figure 5:
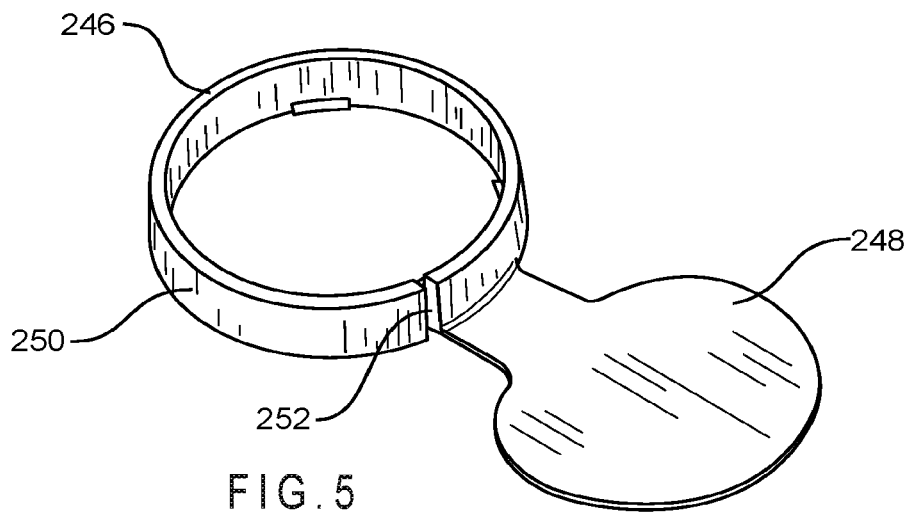
FIG. 5 shows a perspective view of an exemplary embodiment of a retaining ring.

As depicted by FIG. 4, junction 138 may (with reference to the presently-disclosed embodiments) comprise a silicone or rubber O-ring 140 (latex rubber may be acceptable, but generally less preferable than synthetic rubber, such as—for example—ethylene propylene diene monomer (M-class) rubber). O-ring 140 is preferably made of a material suitable for undergoing sterility operations and for use in a sterile medical environment. O-Ring 140 may, for example, be a Parker Hannifin, Shore A 70 durometer EPDM compound E3609-70 O-ring, but it is not limited to this model or these particular specifications. The O-ring 140 preferably provides an air-tight seal at junction 138 between inner surface 136 of widened body 120 and outer surface 34 of mouth 114. The O-ring 140 may be seated in a groove around the outer surface of mouth 114. A groove may be additionally or alternatively incorporated into the inner surface of widened body 120. It is noted that O-ring 140 could alternatively be placed in another suitable location for providing a sufficient seal, such as just below (i.e., just proximally) of the elastomeric cap 114. However, a groove is not required. In other embodiments, a bump or bead extending radially outward from surface 34 or mouth 14 may be provided, which may be molded or otherwise formed on container 12, as depicted by FIG. 2. In this embodiment, an O-ring may be provided directly proximally or distally of the described bead, which may operate to hold the O-ring in place.

O-ring 140 may be compressed between an inner surface 136 and outer surface 134. This compression may act to ensure an air-tight seal to fluidly isolate the space defined by the elastomeric cap 116 from external conditions 142. Further, widened body 120 may be slightly tapered at its proximal end such that the compression of O-ring 140 increases as widened body 120 moves proximally into engagement with mouth 114. Alternatively or additionally, the distal end of mouth 114 may be tapered. In a strongly preferred embodiment, described in further detail below, a silicone O-ring 140 is provided without any adhesive in a manner that still removably secures a fluid-patent (most-preferably air-tight) seal between the elastomeric cap 116 and the bottle 112, where the cap 116 can be removed from and resealed to the bottle 112, or to a second, similarly—or identically—constructed bottle (not shown) without damaging the O-ring 140.

The shape (e.g., the taper) of widened body 120 may force outer surface 134 and inner surface 136 to make contact when elastomeric cap 116 is engaged with mouth 114. The contact may create a point or area of friction that operates to sufficiently secure the elastomeric cap 116 to the mouth 114. The compressed O-ring 140, when squeezed between surfaces 134 and 136, may also provide this securing friction. Any other suitable securing means may be used. When in an engaged state, elastomeric cap 116 is preferably sufficiently secured to bottle 112 such that it will not unintentionally fall out of engagement during a drainage procedure. The vacuum in the bottle interior 113 may provide an additional force on elastomeric cap 116 in the proximal direction when frangible seal 132 is broken. Further, an adhesive, such as a silicone gel, may be applied either during the initial assembly or prior to use at junction 138.

While an adhesive can be used even in embodiments with an O-ring, it may be desirable in some circumstances to forgo using a setting adhesive. For example, it may be useful to remove elastomeric cap 116 prior to (or even during) normal operation. As described herein, it also may be desirable to provide a user, such as a patient, with the ability to engage and unengaged elastomeric cap 116 from container 112 without the help from a medical professional. The use of an O-ring is advantageous over embodiments requiring the application of an adhesive due to the simplicity of the engagement operation. The O-ring may eliminate the often difficult, often unsanitary task of providing a suitable amount of an adhesive to components before a drainage procedure.

In some cases, it is desirable to inspect the frangible seal 132 prior to using the drainage system 110. The friction between the elastomeric cap 116 and bottle 112 may therefore be easily capable of being overcome by a user, such as a nurse or physician, particularly when the frangible seal 132 is intact. This may also give a user the ability to remove elastomeric cap 116 from a container 112, which allows the substitution of one container for another without removing the drainage line 26 (not shown) from communication with a patient. It may further provide the ability to select a particular drainage container in a medical facility immediately prior to beginning the drainage process, for example to select a proper size, vacuum level, etc. This gives a user the ability to select between multiple components to customize or adapt the drainage system 110 for optimal performance based on real-time conditions.

It is often necessary or desirable to visually inspect a frangible seal or other components located adjacent to the junction before and during use of a drainage system 10. Such inspection can bring to light damaged components, improper operation, insufficient vacuum levels, etc. In prior designs, particularly those where a elastomeric cap is secured to a bottle with a setting or drying adhesive, it may be necessary to provide a elastomeric cap 20 made of a transparent material to facilitate these inspections. In particular, the cap may need to be transparent to facilitate visual inspection of the frangible seal 32 in order to make certain that it is intact so that the vacuum provided in the container 12 will provide the desired functionality. A design utilizing an O-ring, as depicted by FIG. 4, may be advantageous for the ability to use a transparent, a translucent, or an opaque elastomeric cap 116. To illustrate, an elastomeric cap 116 may be removed from a bottle 112, thereby allowing a user to inspect the inner components of the elastomeric cap 116 and the components located at the distal end of container 112. The elastomeric cap 116 may then be re-engaged with a container 112 by the user in the manner described above—each without damaging any components. This provides multiple options for inspection, as well as the possibility for ready movement and immediate use of the elastomeric cap (with a second/different bottle) in the event a bottle to which it was connected has a damaged membrane seal or other flaw, where the prior art use of adhesive would make this a more time-consuming process or even require disposal of the entire assembly of the elastomeric cap with the bottle.

An embodiment with an O-ring also provides several manufacturing and assembly advantages. For example, an adhesive such as a silicone gel may be difficult to apply consistently uniformly to the outer surface of a mouth of a bottle (and/or the inner surface of the cap) for facilitating the securing of an elastomeric cap to the mouth portion, resulting in high variability during the assembly process and a large number of faulty or scrap parts. O-rings, on the other hand, are easy to install consistently without the use of complex machinery and generally come in a pre-manufactured form within small dimensional tolerances and with uniform physical properties. The rate of leakage or failure therefore may be substantially smaller when using an O-ring. For example, in a test run of bottles assembled according to the presently-described embodiments, 149 of 150 bottles were successfully assembled with an intact membrane seal of the bottle mouth and with intact seal of the elastomeric cap to the bottle. Use of the presently-described O-ring system reduces manufacturing time, complexity, and expense, all of which provide advantages over the prior art that would not readily be predicted by those having skill in the art, and which provide needed efficiencies in the production of medical equipment. This O-ring system also provides for the ability to use an elastomeric cap and drainage line with more than one bottle (e.g., if a first bottle's seal is damaged or its vacuum is otherwise compromised, the bottle can readily be removed and replaced, or a bottle that is used and filled up may be replaced, each without having to remove the drainage tube from the patient).

A drainage system with an O-ring may also cost substantially less than other embodiments. To illustrate, a single silicone or EPDM O-ring of a type preferably used for embodiments disclosed herein generally costs approximately 50% of the cost of a suitable amount of a suitable silicone adhesive needed to secure and permanently seal an elastomeric cap to a bottle, while providing a more consistently reliable uniform seal. Using O-rings as an alternative may also reduce the need to purchase and maintain costly manufacturing equipment (e.g., silicone gel dispensers), and the highly-consistent assembly associated with the O-ring rather than the silicone adhesive may reduce expenses related to the number of generated scrap parts. Stated differently, the use of the presently-described O-ring system provides several advantages—including cost, device component exchangeability, and device inspectability—as compared to the prior art silicone adhesive assembly.

Referring to FIGS. 5-8, embodiments of a drainage system may include a retaining ring 246 with a constricting portion 250. Retaining ring 246 is not limited to any particular material, but an exemplary material may be a random copolymer polypropylene or polyethylene. Retaining ring 246 may have one or more weakened areas 252. Weakened area 252 may be embodied as a perforated section, a weakened pinch-joint (as shown), etc. Preferably, weakened area 252 is configured to have a lower critical strength or breaking strength than the remainder of constricting portion 250. A handle or tab 248 may be provided and configured to allow a user to provide the necessary force to break retaining ring 246 at weakened area 252 by pulling on tab 248.

Figure 6:
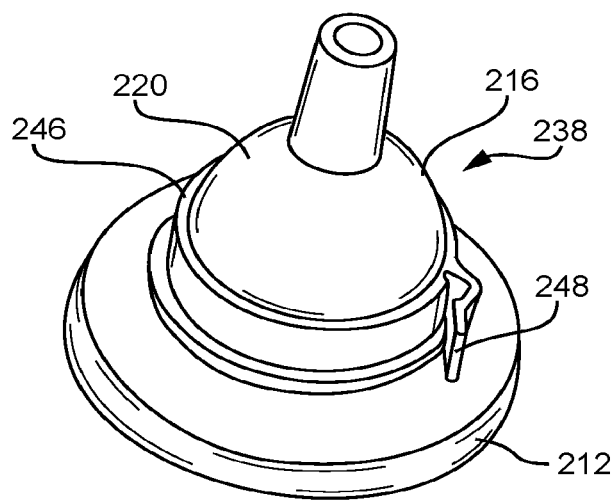
FIG. 6 shows a perspective view of a drainage system comprising a retaining ring circumferentially engaging an elastomeric cap.
Figure 7:
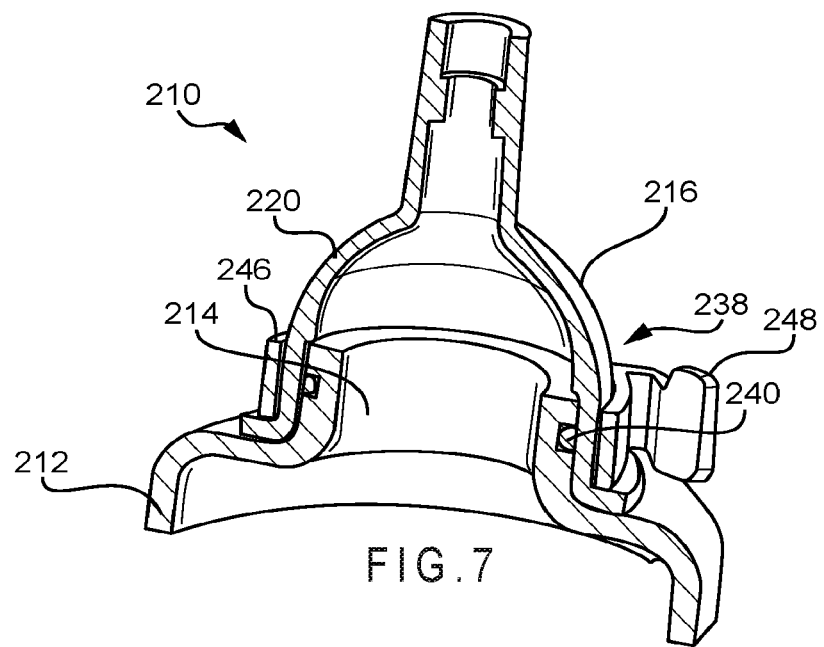
FIG. 7 shows a perspective cutout view of a drainage system comprising a drainage ring.
Figure 8:
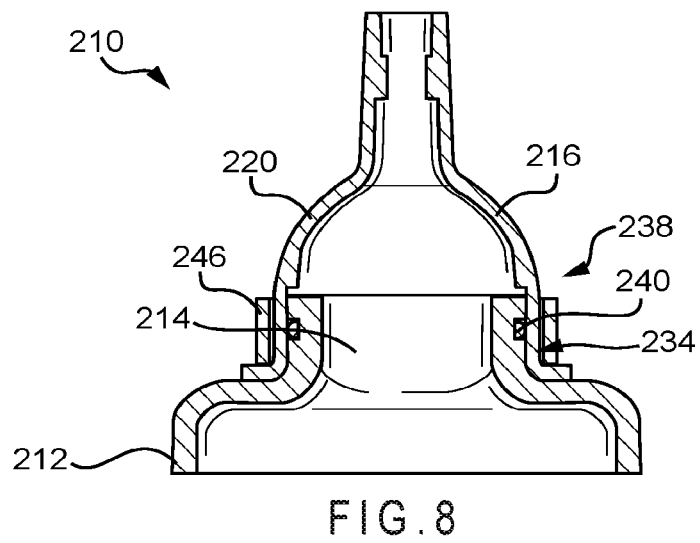
FIG. 8 shows a front parallel projection cutout view of a draining system comprising a drainage ring and an O-ring.

As depicted by FIG. 6, retaining ring 246 is configured to circumferentially engage elastomeric cap 216. Retaining ring 246 may be tightly wrapped around the outside of widened body 220, thereby providing a constricting force to retain elastomeric cap 216 in engagement with mouth 214 of container 212. As best shown by FIG. 7 and FIG. 8, retaining ring 246 is preferably wrapped around elastomeric cap 216 adjacent to junction 238 and is radially aligned circumferentially coaxially around and just outside of O-ring 240 to provide an inward constricting force on elastomeric cap 216 and a reliably consistent uniform seal between the container, O-ring, and cap to patently maintain vacuum. This constriction may provide increased tightness or compression of O-ring 240, which may improve the performance of the seal at junction 238. The constriction provided by retaining ring 246 may make it difficult (or essentially impossible) for a user to pull elastomeric cap 216 out of engagement with container 212 when it is active.

When a user pulls on tab 248 with a force sufficient to break retaining ring 246, retaining ring 246 seizes providing the constricting force. Elastomeric cap 216 may then be removed from engagement with container 212 relatively easily, and consistently below the desirable maximum threshold of force for a typical user. Other embodiments of a drainage system may alternatively include another type of removable device configured to provide constriction around elastomeric cap 216, such as a snap-fit belt, a removable tie or wrap, a band clamp, etc.

In some embodiments, retaining ring 246 may be pre-installed at junction 238 and providing constriction prior to handing by a user. This may require that elastomeric cap 216 is pre-engaged with container 212 prior to the handling by a user. Alternatively, retaining ring 246 may be provided with elastomeric cap 216 but separately from container 212. Here, for example, the retaining ring 246 may initially surround elastomeric cap 216 (or other proximal components, such as a drainage line), but be located proximally of widened body 220. After elastomeric cap 216 is moved into engagement with container 212, a user may slide retaining ring 246 distally into position for providing the herein described constriction.

Referring to FIG. 4, the drainage system 110 may include a stop 160 configured to contact a shoulder 162 of container 112. In one embodiment, which may include a tapered widened body 120 as described herein, elastomeric cap 116 comprises stop 160 configured to communicate with shoulder 162 such that it abuts shoulder 162 when a proper level of engagement with container 112 is achieved. In other words, stop 160 and shoulder 162 may prevent elastomeric cap 116 from sliding too far in the proximal direction when moving into engagement. This can prevent damage to O-ring 140, undesired warping or jamming of components near junction 138, etc. The operation of stop 160 may further provide an indication to the user that a sufficient level of engagement is achieved, thereby signaling the assurance of sufficient securing and sealing at junction 138. Although various embodiments of the invention have been described, it will be apparent to those of ordinary skill in the art that many more embodiments and implementations are possible that are within the scope of the invention. For instance, steps of a method as displayed in the figures or reflected in the claims do not require a specific order of execution by way they are presented, unless specified. The disclosed steps are listed as exemplary such that additional or different steps may be executed or the steps may be executed in a different order. Those of skill in the art will appreciate that embodiments not expressly illustrated herein may be practiced within the scope of the claims, including that features described herein for different embodiments may be combined with each other and/or with currently-known or future-developed technologies while remaining within the scope of the claims.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A drainage system comprising:
    a container having an interior, a mouth, the mouth comprising an outer surface and an opening;
    a frangible seal covering the opening, the frangible seal having a surface perpendicular to the outer surface of the mouth;
    a cap secured to the mouth and in fluid communication with a drainage line, the cap comprising a body having an inner surface configured to engage with the outer surface of the mouth and a sleeve that is monolithic with the body and that extends away from the mouth;
    an O-ring located around the mouth and between the outer surface of the mouth and the inner surface of the cap such that the O-ring forms a fluid seal between a space defined by the cap and environment surrounding the drainage system; and
    a retaining ring formed separately from the cap that is configured to be radially aligned with the O-ring and coaxial with the O-ring to provide a constricting force on the O-ring;
    wherein the retaining ring comprising a constricting portion extending around the mouth having a top facing terminal edge, an opposite, bottom facing terminal edge and a face facing the body of the cap, the face of the constricting portion is entirely contiguous with the body of the cap from the top facing terminal edge to the bottom facing terminal edge.

2. The drainage system of claim 1, wherein the retaining ring has a constant inner diameter.

3. The drainage system of claim 1, further comprising a spiked tube positioned at least partially within the cap and configured to pierce the frangible seal.

4. The drainage system of claim 3, wherein a vacuum is transferred from the interior of the container to the space defined by the cap, and the interior of the container is in patent fluid communication with the space defined by the cap when the frangible seal is pierced.

5. The drainage system of claim 1, wherein the body of the cap is tapered.

6. The drainage system of claim 1, wherein the retaining ring includes a weakened area with a lower critical strength than an adjacent area such that the retaining ring breaks at the weakened area in response to an input force from a user.

7. The drainage system of claim 1, wherein the interior of the container holds a vacuum.

8. The drainage system of claim 1, wherein a stop extends outwardly from the mouth along a shoulder where the container widens to an increased internal volume and the retaining ring rests on the stop when the retaining ring is radially aligned with the O-ring and coaxial with the O-ring.

9. A drainage system, the drainage system comprising:
    a container having a mouth with a first surface surrounding an opening;
    a cap secured to the mouth that comprises a body and a sleeve that is monolithic with the body and extends away from the mouth, the cap having an inner surface configured to engage with the first surface of the mouth;
    a drainage line located distally of the cap and in fluid communication with a space defined by the cap; and
    an O-ring located between the first surface and the inner surface and configured to retain a vacuum within the drainage system; and
    a retaining ring formed separately from the cap that is radially aligned with the O-ring and coaxial with the O-ring to provide a constricting force on the O-ring;
    wherein the retaining ring comprising a constricting portion extending around the mouth having a top facing terminal edge, an opposite, bottom facing terminal edge and a face facing the body of the cap, the face of the constricting portion is entirely contiguous with the body of the cap from the top facing terminal edge to the bottom facing terminal edge.

10. The drainage system of claim 9, the drainage system further comprising:
    a frangible seal covering the opening and maintaining the vacuum within the container while the frangible seal is intact; and
    a tube located at least partially within the cap, the tube having a spike, wherein the spike is configured to pierce the frangible seal.

11. The drainage system of claim 9, wherein the O-ring is configured to provide a friction force for securing the cap to the mouth.

12. The drainage system of claim 9, wherein the cap further comprises a tapered portion.

13. The drainage system of claim 9, wherein the cap is opaque.

14. The drainage system of claim 9, wherein an interior of the container contains the vacuum.

15. The drainage system of claim 9, wherein the drainage line provides fluid communication with a collection device.

16. The drainage system of claim 9, wherein a stop extends outwardly along a shoulder where the container widens to an increased internal volume and the retaining ring rests on the stop when the retaining ring is radially aligned with the O-ring and coaxial with the O-ring.

17. A method for draining a fluid from a patient with a drainage system, the method comprising:
    placing a distal end of a drainage line into contact with a target fluid, wherein a proximal end of the drainage line contacts and provides for fluid communication with a cap that includes an inner cap surface, the cap comprising a body and a sleeve that is monolithic with the body and that extends away from outward from the body in a direction that is perpendicular to an outer surface of a mouth of a drainage container;

moving the body proximally into engagement with the mouth of the drainage container such that an O-ring provides a seal between an outer surface of the mouth and the inner cap surface; and sliding a retaining ring proximally over the sleeve and the body of the cap such that the retaining ring is radially aligned with the O-ring and coaxial with the O-ring to provide a constricting force on the O-ring;

wherein the retaining ring comprising a constricting portion extending around the mouth having a top facing terminal edge, an opposite, bottom facing terminal edge and a face facing the body of the cap, the face of the constricting portion is entirely contiguous with the body of the cap from the top facing terminal edge to the bottom facing terminal edge.

18. The method of claim 17, wherein the cap is opaque.

19. The method of claim 17, further comprising moving the cap distally out of engagement with the mouth and later moving the cap proximally into sealing engagement around a mouth of a second container.

* * * * *